(12) United States Patent
Wiktor et al.

(10) Patent No.: US 11,793,914 B2
(45) Date of Patent: Oct. 24, 2023

(54) MEDICAL SYSTEM FOR MONITORING USING RADAR WAVES

(71) Applicant: Fresenius Medical Care Deutschland GmbH, Bad Homburg (DE)

(72) Inventors: Christoph Wiktor, Gelnhausen (DE); Andreas Röse, Frankfurt (DE); Benedict Glaser, Schweinfurt (DE); Manuel Weikert, Frankenwinheim (DE); Gerome Fischer, Weberstedt (DE); Martin Urban, Güntersleben (DE); David Hannes, Frankfurt (DE); Pascal Kopperschmidt, Dittelbrunn (DE); Felix Wege, Aachen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 290 days.

(21) Appl. No.: 17/194,546

(22) Filed: Mar. 8, 2021

(65) Prior Publication Data

US 2021/0369928 A1    Dec. 2, 2021

(30) Foreign Application Priority Data

May 29, 2020   (DE) .......................... 102020114502.0

(51) Int. Cl.
*A61M 1/16*     (2006.01)
*A61M 1/36*     (2006.01)

(52) U.S. Cl.
CPC ........ *A61M 1/1601* (2014.02); *A61M 1/3659* (2014.02); *A61M 2205/35* (2013.01);
(Continued)

(58) Field of Classification Search
CPC .............. A61M 1/1601; A61M 1/3659; A61M 2205/35; A61M 2205/502;
(Continued)

(56) References Cited

U.S. PATENT DOCUMENTS 5,647,373 A     7/1997  Paltieli
2008/0119716 A1 *  5/2008  Boric-Lubecke .... A61B 5/7225
                                                600/407
(Continued)

FOREIGN PATENT DOCUMENTS

DE     102009005110 B3    11/2010
DE     102011083408 A1     3/2013
(Continued)

OTHER PUBLICATIONS

Ahmad et al., "Clinical Review: A Review and Analysis of Heart Rate Variability and the Diagnosis and Prognosis of Infection," *Critical Care*, 13 (2009).
(Continued)

*Primary Examiner* — Hayden Brewster
(74) *Attorney, Agent, or Firm* — Leydig, Voit & Mayer, Ltd.

(57) ABSTRACT

A medical system, usable for example in connection with a dialysis apparatus, may utilize radar waves for monitoring a patient, a medical area, or an object. The medical system includes at least one sending device for sending radar waves, and at least one receiving device for receiving reflected radar waves. The medical system further includes an evaluation unit for evaluating the reflected radar waves which have been received by the at least one receiving device, resulting in obtaining a result, and an output device for outputting the result or a signal based on the result.

25 Claims, 7 Drawing Sheets

(52) U.S. Cl.
CPC ... *A61M 2205/502* (2013.01); *A61M 2205/60* (2013.01); *A61M 2209/088* (2013.01); *A61M 2230/04* (2013.01); *A61M 2230/63* (2013.01)

(58) Field of Classification Search
CPC ........ A61M 2205/60; A61M 2209/088; A61M 2230/04; A61M 2230/63; A61M 1/3655; A61M 2205/3306; A61M 2205/3317; A61M 2205/3368; A61M 1/3656; A61M 2205/52; A61M 2230/62; G16H 20/40; G16H 40/63; G01S 13/88; G01S 13/50; G01S 13/86

See application file for complete search history.

(56) References Cited

U.S. PATENT DOCUMENTS

| | | | |
|---|---|---|---|
| 2010/0152600 A1* | 6/2010 | Droitcour | A61B 5/1113 600/534 |
| 2010/0241009 A1 | 9/2010 | Petkie | |
| 2012/0022348 A1 | 1/2012 | Droitcour et al. | |
| 2015/0065916 A1 | 3/2015 | Maguire et al. | |
| 2015/0141794 A1 | 5/2015 | Foo | |
| 2016/0249990 A1 | 9/2016 | Glozman et al. | |
| 2018/0221560 A1 | 8/2018 | Niemetz et al. | |
| 2019/0159960 A1 | 5/2019 | Nakata et al. | |
| 2019/0298208 A1 | 10/2019 | Weinstein et al. | |
| 2019/0374700 A1 | 12/2019 | Kopperschmidt et al. | |
| 2020/0121215 A1 | 4/2020 | Hyde et al. | |

FOREIGN PATENT DOCUMENTS

| | | |
|---|---|---|
| DE | 112014000372 T5 | 10/2015 |
| DE | 102017102169 A1 | 8/2018 |
| DE | 102018213626 A1 | 2/2020 |
| WO | WO 2019/021614 A1 | 1/2019 |

OTHER PUBLICATIONS

Cao et al., "Heart ID: Human Identification Based on Radar Micro-Doppler Signatures of the Heart Using Deep Learning," *Remote Sens.*, 11 (2019).

* cited by examiner

MEDICAL SYSTEM FOR MONITORING USING RADAR WAVES

CROSS-REFERENCE TO RELATED APPLICATIONS

Priority is claimed to German Patent Application No. DE 102020114502.0, filed on May 29, 2020, the entire disclosure of which is hereby incorporated by reference herein.

FIELD

Exemplary embodiments of the present invention relate to a medical set or system and to a method for monitoring a patient, a medical area and/or an object using radar waves.

BACKGROUND

Today's modern health care system enables unprecedented medical care for patients, not least through the use of complex diagnostic and blood treatment apparatuses. The required patient safety in connection with such complex diagnostic and blood treatment apparatuses and increasing automation in everyday hospital life may usually only be guaranteed if the patient to be treated, the diagnostic and blood treatment apparatus used and/or the interaction between patient and apparatus can be closely monitored. This monitoring may include the unambiguous or distinct identification of a patient as well as an unambiguous or distinct location and the determination of his position.

An apparatus for extracorporeal blood treatment by dialysis may be mentioned as an example of a complex blood treatment apparatus from practice. Here, blood is taken from the patient and led extracorporeally along a blood circuit and through a blood filter of the dialysis apparatus. During the blood treatment session carried out in this way, the treatment may be influenced by a plurality of treatment parameters which are adjustable at the dialysis apparatus, inter alia by changing flow rates and/or drug dosages. The patient should remain under observation during such a treatment, for example to detect complications such as an incorrect cannulation at an early stage or to be able to react appropriately to disturbances of the patient's well-being or state, e.g. caused by or associated with a drop in blood pressure.

SUMMARY

In an exemplary embodiment, the present invention provides a medical system for monitoring a patient using radar waves. The medical system includes: a transmitter configured to emit radar waves using one or more predetermined frequencies; a receiver configured to receive reflected radar waves; a processor configured to evaluate the reflected radar waves received by the receiver to determine a position or a position change of the patient's body or a part thereof; and an output interface for outputting a result of the evaluation.

In another exemplary embodiment, the present invention provides a medical system for monitoring an object using radar waves. The medical system includes: a transmitter configured to emit radar waves using one or more predetermined frequencies; a receiver configured to receive reflected radar waves; a processor configured to evaluate the reflected radar waves received by the receiver to determine a position or a position change of the object; and an output interface for outputting a result of the evaluation.

In yet another exemplary embodiment, the present invention provides a medical system for monitoring a medical area using radar waves. The medical system includes: a transmitter configured to emit radar waves using one or more predetermined frequencies; a receiver configured to receive reflected radar waves; a processor configured to evaluate the reflected radar waves received by the receiver to determine a characteristic of the medical area; and an output interface for outputting a result of the evaluation.

BRIEF DESCRIPTION OF THE DRAWINGS

Exemplary embodiments of the present invention will be described in even greater detail below based on the exemplary figures. The invention is not limited to the exemplary embodiments. All features described and/or illustrated herein can be used alone or combined in different combinations in embodiments of the invention. Features and advantages of various embodiments of the present invention will become apparent by reading the following detailed description with reference to the attached drawings which illustrate the following.

DETAILED DESCRIPTION

Figure 1:
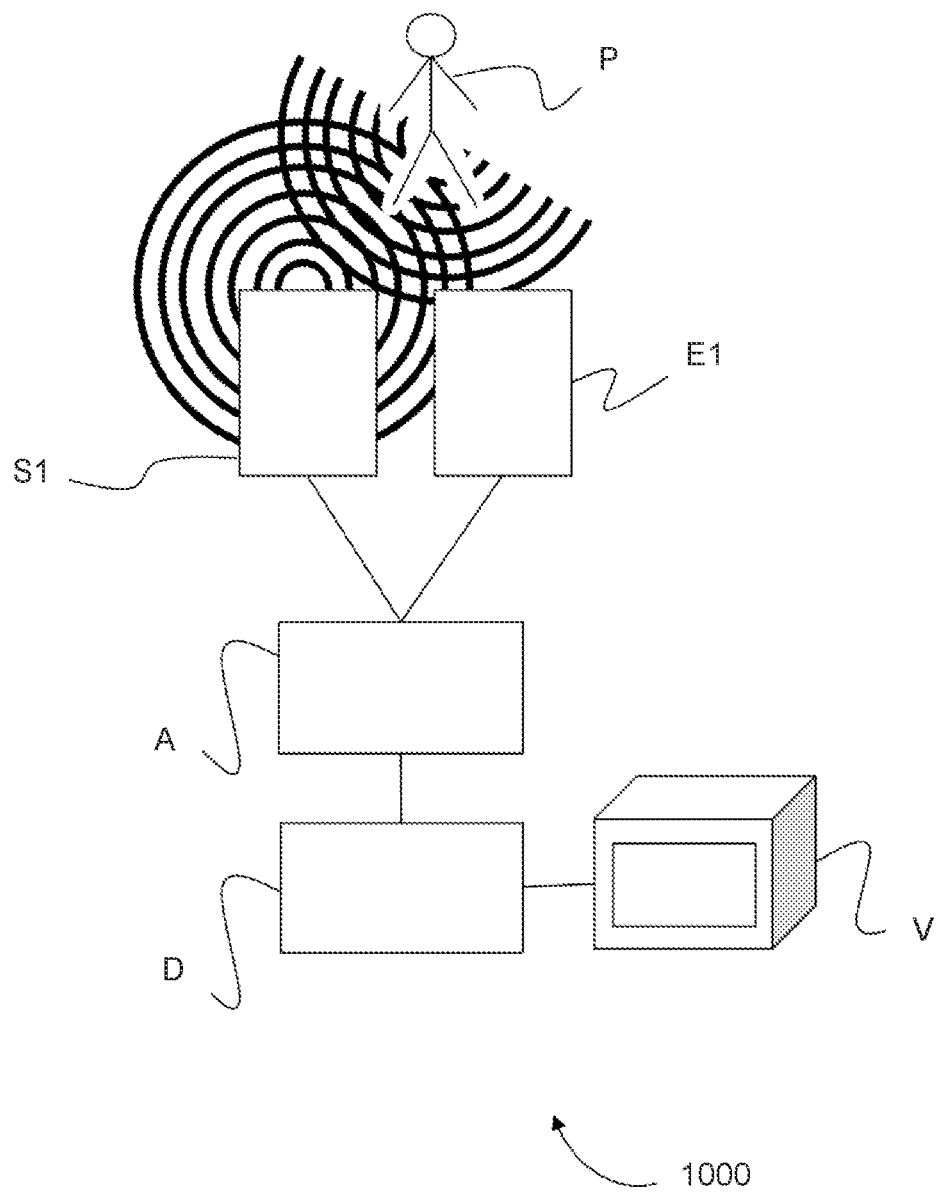
FIG. 1 shows a simplified illustration of a medical set according to the present invention in a first embodiment.

Exemplary embodiments of the present invention provide a medical set for monitoring a patient and a method.

In an exemplary embodiment, the present invention provides a medical set or system (hereinafter also briefly: set) for monitoring a patient and/or a medical area using radar waves. The set comprises at least one first sending device (e.g., at least one transmitter) for emitting radar waves, at least one first receiving device (e.g., at least one receiver) for receiving reflected radar waves, at least one evaluation unit (e.g., at least one processor) for evaluating the radar waves received by the first receiving device, and an output device (e.g., a display, a transmitter, a transceiver, or a communication interface) for outputting the result or at least a signal based on said result. The evaluation unit is preferably programmed to achieve a result of the evaluation (herein also: evaluation result), to make it available and to transmit it to the output device.

The aforementioned devices and units may be implemented in a common component or distributed over several components, and they may be provided together or separate from each other.

When in use, the evaluation unit and the output device may be in signal communication with each other, or be prepared for this, in a conductor-bound or cable-bound manner, wirelessly or in another way.

In a further exemplary embodiment, the present invention provides a method for monitoring a patient and/or a medical area by radar waves. The method comprises the following steps:
a) providing a medical set according to an exemplary embodiment of the present invention;
b) emitting radar waves by the first sending device at least in the direction towards the patient and/or towards the medical area, or starting from a first location;
c) receiving radar waves, reflected by the patient and/or by the medical area, using the first receiving device;
d) evaluating the radar waves received by the first receiving device using the evaluation unit suitable for evaluating the reflected radar waves resulting in obtaining a result or an evaluation result; and/or
e) outputting the result or a signal based on said result.

Whenever a suitability or a method step is mentioned herein, exemplary embodiments of the present invention may also encompass a corresponding programming or a configuration of a suitable device or of a section thereof, in particular for executing the relevant method step.

Embodiments according to the present invention may comprise one, several or all of the following features in any combination, unless this is recognized as being technically impossible by the person skilled in the art.

In all the aforementioned or following statements, the use of the expression "may be" or "may have" and so on is intended to illustrate exemplary embodiments according to the present invention.

Whenever numerical words are mentioned herein, the person skilled in the art shall recognize or understand them as indications of numerical lower limits. Unless it leads the person skilled in the art to an evident contradiction, the person skilled in the art shall comprehend for example the specification of "one" as encompassing "at least one". This understanding is also equally encompassed by exemplary embodiments of the present invention as the interpretation that a numerical word, for example, "one" may alternatively mean "exactly one", wherever this is evidently technically possible for the person skilled in the art. Both are encompassed by exemplary embodiments of the present invention and apply to all numerical words used herein.

What is stated here regarding blood treatment apparatuses also applies undiminished to treatment apparatuses with which it is not the patient's blood that is treated. It is therefore also encompassed by exemplary embodiments of the present invention to replace the term "blood treatment apparatus" by the broader term "treatment apparatus".

A sending device for radar waves, as used herein, is, for example, a device which emits a so-called primary signal as a bundled electromagnetic wave. A receiving device for radar waves, as used herein, is, for example, a device which receives echoes reflected from objects or, in the case of transmission, the attenuated primary signal as a secondary signal. The secondary signal may be evaluated according to predetermined criteria.

A radar wave may be an electromagnetic wave or electromagnetic radiation; it may be a wave of coupled electric and magnetic fields. Examples of electromagnetic waves are radio waves, microwaves, thermal radiation, light, X-rays and gamma radiation. Electromagnetic waves in a vacuum are transverse waves. The interaction of electromagnetic waves with matter depends on their frequency.

A sending device of a set according to exemplary embodiments of the present invention may be configured to emit radar waves with a frequency f of 1 to 300 GHz, which corresponds to a wavelength of approximately 30 cm to 1 mm.

Radar waves can be (near field) radar waves.

In some embodiments, the evaluation unit is programmed to determine a position or a position change of the patient's body or of the medical personnel (doctor, caregiver, nurse, etc.) or a part thereof, e.g. a limb, or an object. The object may be a medical object, for example a cannula or a plaster.

Corresponding outputs, such as a graphical output, may be provided by an output device, for example by a visualization device as discussed below. The output device and visualization device may be implemented in a common component or distributed over several components, and they may be provided together or separate from each other.

A detection of a position change may be carried out by two examinations of the same object, of the patient, of the medical staff etc. at different times using the set and the subsequent comparison of the evaluation results of these examinations.

A detection of a position or change in position may be absolute (e.g. measured on a stationary coordinate system) or relative (e.g. related to a further, non-stationary structure, such as the detected position from a previous investigation, as described above).

The detection of the position change/position of a patient enables a useful shift, expansion or correction of limit values (e.g. alarm limits for pressure monitoring) at a medical technical device (e.g. a dialysis machine).

In a further embodiment, the object, whose position or position change is determined, for example a cannula whose position in space or whose position change, which may also be understood here as a change in location, is of interest. The location/position in space may hereby, for example, be determined absolutely (e.g. by determining spatial coordinates) or in a relative manner (e.g. relative to the crook of the arm in which the cannula is inserted).

For example, it may be of interest to determine—for a patient whose vascular system has been punctured with a cannula through which, for example, blood is taken or a solution is administered—whether the patient or the patient's arm has moved relative to a monitoring at a previous point in time (e.g. by the patient repositioning himself, sitting on the treatment stretcher, turning in bed, etc.), and if so, how the patient or the patient's arm has moved.

Alternatively or in addition, it may be of interest whether the patient lies (height above the floor), sits, stands or has straightened up (change over time), as this may influence, for example, the hydrostatic pressure component in the arterial pressure and the venous pressure, and the knowledge about the patient's posture may explain certain pressure phenomena and possibly lead to adjustments in limit values, assessments, etc. If it has been, for example determined by a set according to exemplary embodiments of the present invention, how the patient is positioned, or whether he has changed his position, conclusions may then be drawn from this with regard to, for example his blood pressure, its changes, etc. In some embodiments, on the basis of such a position determination or detection of position change, the limit values for the arterial and/or venous pressure are adjusted (based on the knowledge thus obtained about the hydrostatic component part of the measured pressure value). Alternatively or in addition, the limit values or limit value windows are adjusted or expanded for the duration of the position change.

In some embodiments, since such position detection or detection of a position change may detect even a fall of the patient or the standing up of a patient, for example, being connected to an extracorporeal blood circuit (also: blood tubing set), the output device may be programmed to output information or an alarm to the personnel and/or to trigger an alarm state in the blood treatment apparatus.

Detected position changes may thus advantageously be taken into account. The knowledge about them may advantageously contribute to fewer false alarms than before, due to for example harmless changes in the patient's position.

Since further limit values may be set more narrowly with detected position or position change, the quality or the information content of the pressure monitoring may be increased. A stenosis or dislocation of the venous needle can be detected at an early stage.

In some embodiments, the evaluation unit is programmed to determine vital data, e.g. heart rate, pulse wave propagation, respiratory rate, or any other state of the patient.

In several embodiments, the evaluation unit is programmed to determine a state of at least one blood vessel.

The state may be determined by examining the movement of one or more of the patient's vessels by the medical set, e.g. during a predetermined duration or event, which may be based in particular on the cardiac phase (e.g. during systole, between two cardiac cycles (e.g. from the beginning of a systole to the beginning of the following systole), over the duration of one cardiac cycle segment, for example, across systole, etc.).

The state may be evaluated using records or in real time.

It may be provided to compare the state with stored states in order to achieve a result.

A state may consist of or comprise data that allow a visual representation, or it may be represented visually.

A state may consist of or comprise key figures. Key figures may be descriptions of values, tissue scores and the like, which allow a description of the relevant tissue or of its behavior, such as, for example, its lateral displacement or local expansion during the cardiac cycle, e.g. during its systole.

The state may be determined or evaluated in comparison with or by using patterns.

The patterns may be from the same patient and, for example, from previous examinations of that patient. Alternatively, the records may have been gathered from a group of patients or a patient collective.

The result of the comparison may provide information about the state of the vessel or a section thereof, e.g. a shunt, Cimino shunt, or a Cimino-Brescia fistula, or its vascular wall, such as statements about its elasticity, permeability, free lumen cross-sectional area, amount of movement during the heart phase under consideration, wall thickness, or the like.

The result of the comparison may be output as a result or as part of the result using the output device.

The output device may be configured in an exemplary embodiment to communicate a notification or an alarm based on the result.

For example, it may be provided in some embodiments to determine changes in respiration rate, respiratory amplitude, heart rate and/or blood pressure. These may be an indicator of circulatory instability (tachycardia, bradycardia), a drop in blood pressure, a shock (identifiable by heart rate variability, increasing heart rate when the system is centralized) or a sepsis (identifiable by measuring the parameters for determining the qSOFA index ("quick Sepsis Related Organ Failure Assessment"), such as, e.g. respiratory rate, Glasgow Coma Score, systolic blood pressure) and, therefore, serve for (early) detection of the same.

For this purpose, the vital parameters of the patient, e.g. during his treatment, e.g. a dialysis treatment, are in some embodiments determined in a contactless manner or without contact using a sensor (e.g. continuously). In several embodiments, the set is programmed for this purpose.

If vital parameters or other values determined by the set deviate from predetermined limit values, limit ranges or other specifications, or if predetermined criteria are not met or are met for the first time, it may be provided to take or initiate suitable measures automatically. Limit values or limit ranges are violated, for example, if individual thresholds (e.g. blood pressure, heart rate, respiratory rate) are exceeded or fallen below, or if combinations of values as combined conditional thresholds (e.g. movement rate smaller/larger than a limit value, heart rate above a limit value and respiratory amplitude below limit value) are exceeded or fallen below.

Suitable measures may be or may include alerting nursing staff, automatically changing treatment parameters (for example changing the ultrafiltration rate (in short: UF rate), the dialysis liquid flow of a blood treatment apparatus, the temperature, etc.), observing the effect on the vital parameters, initiating readjustment of the change, monitoring feedback, and/or releasing a bolus.

The following measures may be taken to increase the quality/robustness of the measurement data:

For example, a correlation of vital data with or to machine data of the blood treatment apparatus, e.g. the dialysis machine (pressure signals, blood pressure measurement data, UF rate, blood flow) may be determined and used. This provides a comprehensive and continuous picture of the patient status (circulation stability, intensity of movement, well-being). The vital data measured contactlessly may supplement data that were measured in a different way than by a set according to exemplary embodiments of the present invention, or serve as the basis for an interpolation.

It is also possible to calibrate or verify an adjustment of the sensor or of the vital data with the help of machine data. In this, for example, sensor data of a conventional blood pressure measurement are related to the recorded vital data (here: blood pressure) or initially calibrated/verified via this data e.g. using a Blood Pressure Monitor (BPM) of the blood treatment apparatus.

Exemplary embodiments of the present invention also include the use of the set to capture vital data, preferably automatically, which serve to build up redundancies. Thus, for example, the blood pressure measurement, which is carried out automatically by the blood treatment apparatus, mostly at the extracorporeal blood circuit, may be monitored for plausibility and/or compared with a pulse measurement, carried out by a set according to exemplary embodiments of the present invention in order to increase the safety for the patient.

In this way, complete monitoring of the patient is advantageously possible without being in constant direct contact with said patient. Furthermore, critical conditions may be detected early or at least quickly. The measurement may also be automated. Monitoring is therefore also possible in an outpatient environment and even at home.

Exemplary embodiments of the present invention may also include recording the state of the patient. For example, the medical set may be programmed to compare measurement results with stored algorithms, patterns or the like. This may, for example, clarify the questions of whether the patient is sleeping or awake, how deep the sleep is and/or what his sleep status is. Sleep patterns may also be determined in general. Monitoring the breathing, which may serve to detect a cardiac or respiratory arrest, may also be included in the recorded states. In case of abnormalities, such as a standstill or a respiratory rate that is too low or too high, an alarm may be issued.

An identification of the overall health state of the patient is possible by automatic evaluation of the sleep phases and/or of his general movement intensity during dialysis over a longer period of time, and a corresponding programming may be provided.

A determination or ascertainment of the patient's state may also provide diagnostic support, for example by diagnosing sleep apnea based on the above-mentioned monitoring or by contributing to the diagnosis or diagnosis result.

Diagnostic indications may be derived from the intensity of movement as an indication of a deterioration of the state of health: if the patient moves less or becomes more nervous, these can be signs of a deterioration of his condition.

The evaluation unit may be programmed to compare a pattern determined by a set according to exemplary embodiments of the present invention with a saved or stored pattern.

In some embodiments, the evaluation unit is programmed to identify a person, e.g. by vital data, body topology, movement patterns, backscattering (see below), etc. The evaluation unit may be used to access stored patterns or data by comparison. The result of the comparison may be output as a result or part of the result using the output device.

According to exemplary embodiments of the present invention, it may be provided to infer the associated patients from the vital data determined or extracted by the evaluation unit. This may be done by comparison with person-specific unique patterns, e.g. heart rhythm (frequency, amplitude). Alternatively or additionally, the identity of the patient may be determined by evaluating a body topology of the patient (e.g. his face) or his movement pattern determined by a sending device and a receiving device.

If the patient is identified in this or in another way, sections in the setup of the blood treatment apparatus and/or patient data may be loaded, determined or selected in a patient-specific manner by the set, for example in connection with the control device of the blood treatment apparatus.

Releasing or calling up settings and sections in the setup of a blood treatment apparatus based on the identification of a person may give different results for patients, nursing staff, or technicians. For example, a nurse may set treatment parameters that are denied to the technician. The technician, in turn, is allowed to access system functions that are not accessible to the caregiver. Advantageously, this calling up and/or the releasing is contact-free and, therefore, hygienic.

Above all, the possibility of identifying a patient may hereby be advantageous without the need for visual images or recordings as reference or comparison patterns or recordings of the patient at the moment of identification. In this, data protection aspects are rather guaranteed. In addition, this type of identification is also advantageously possible at night or in poor lighting conditions.

Further measures to increase security or safety, for example in combination with a further identification device (identification card, code), may also be implemented.

It may be advantageous that an extremely short measuring time (e.g., a few seconds or milliseconds) is sufficient to collect the information needed to identify a person.

In some embodiments, the medical set also comprises a reference object. The latter serves for example to be releasably attached to the patient's body, e.g. as a sticker, label, tag, marker, etc. It is attached as intended so that it may also reflect the radar waves emitted by the sending device.

In some embodiments, the reference object may be provided, for example, in or on the plaster that fixes the cannula at the patient's arm. If the distance between the cannula and the reference object changes, this may be detected and may be of interest.

In these embodiments, the evaluation unit is further programmed to additionally evaluate radar waves reflected by the reference object and received by the at least one receiving device.

The evaluation may include the mathematical establishment or determination of a spatial reference between, for example, the object irradiated by radar waves and the reference object.

For example, it may be of interest how far the arm, in the crook of which a cannula was inserted, has been rotated around e.g. the longitudinal axis of the humerus, as this rotation may impair the correct position of the cannula or the tubing connected to it, which is why it is monitored. The rotation may be determined, for example, by providing a (further) reference object on the upper arm of the punctured arm in addition to the object placed in the forearm or in the crook of the arm (here: cannula). A change in the positions of the object and reference object relative to each other allows a statement about the current rotation of the arm, which may be transmitted as a result of the evaluation from the evaluation unit to the output device, e.g. an alarm device.

In some embodiments, the evaluation unit is programmed to compare, the patterns, intensity or other distinguishing features of the received radar waves, or evaluations based thereon, with reference data or sets, and reference patterns or evaluations based thereon in order to receive a result.

In some embodiments, the reference data or sets and/or the reference patterns are or include data, data sets and/or patterns of predetermined materials, surfaces, surface finishes (such as rough, smooth, dry, moist or wet), reflectance or measure of certain fabrics or liquids, radar waves already received at another time, or evaluations based thereon.

According to exemplary embodiments of the present invention, blood loss, which may lead to moistening or even wetting of bed sheets, plasters, bandages, surfaces, etc., may thus be determined by the medical set based on the surface examination proposed for some embodiments. This may advantageously be done even through a blanket or cover or duvet.

In this, the existence of reflective surfaces, e.g. on the bed level, the emergence of reflective surfaces or the temporal change of the reflective surface may be determined. Liquid films that have formed on a surface may be detected or monitored in this way.

In this, a substance detection is contactless and therefore hygienically possible.

According to exemplary embodiments of the present invention, a programming of the set may also be provided such that substances or the substance properties are recognized on the basis of the reflected radar waves and the knowledge obtained is transmitted e.g. by the output device.

In several embodiments, a set according to exemplary embodiments of the present invention may be used to provide level detection in chambers (air/fluid differentiation), such as the venous drip chamber, the water inlet chamber or in air separation chambers. A detection of the transition between blood/water in an extracorporeal blood circuit may also be provided. Measurement data on the hematocrit (measurement with BVM) in combination with radar sensor data may be collected by a set according to exemplary embodiments of the invention (adjustment of the sensor while knowing the hematocrit value for the individual patient).

In some embodiments, the predetermined surfaces include the patient's skin, a bed linen, or bedding.

The medical set may be programmed, for example, to determine a surface topology using radar waves. The observation that, for example, the reflection of radar radiation depends on the topology of the surface may be used for this purpose.

According to exemplary embodiments of the present invention, it may thus be possible to detect the formation of "goose bumps" on the patient's skin. This may be an indication of a circulatory instability of the patient or of a coldness felt by the patient.

Likewise, the formation of sweat on the skin may be detected, which may also be an indication of a circulatory instability of the patient or an indication of warmth felt by the patient.

Furthermore, the medical set may comprise a thermal camera, by which changes or absolute states of surfaces or areas may be determined or monitored by thermography. For example, moisture heated by radar waves (on surfaces, in or on clothing, in or on dressing material, on the skin, etc.) may cause a local change in temperatures that may be determinable by thermography. The medical set may be programmed to detect such changes or the heat input causing them and may indicate them visually or in some other way. In this, for example, a wet "adhesive" tag may reflect a radar wave or reflect differently than a dry adhesive tag.

Impressions that were previously only recorded by the nursing staff or the patient himself may thus advantageously be recorded automatically, such as sweat on the patient's skin, goose bumps, whether the patient is cold or has circulatory problems, and the like.

In several embodiments, the predetermined tissues are or include one or more blood vessels.

In several embodiments, the predetermined liquids are blood or comprise blood.

In some embodiments, the medical set further comprises at least one second sending device. Thereby, the first sending device is arranged to emit radar waves in a first direction or from a first location, and the second sending device is arranged to emit radar waves in a second direction different from the first direction or from a second location different from the first location. Alternatively or in addition, the first sending device on the one hand and the second sending device on the other hand are arranged spaced apart from each other. They may be housed in a common component or housing, or in separate ones.

In some embodiments, the set further comprises a second receiving device. In these embodiments, the first receiving device is arranged to receive radar waves from a first direction or from a first location, and the second receiving device is arranged to receive radar waves from a second direction different from the first direction or from a second location different from the first location. Alternatively or in addition, the first receiving device on the one hand and the second receiving device on the other hand are arranged spaced apart from each other. They may be housed in a common component or housing, or in separate ones.

In some embodiments, the evaluation unit is programmed to detect, e.g. calculate, a three-dimensional extension of the object, of the patient or or of at least a body section. The patient is irradiated with radar waves by the first, second and/or further sending device. It is thus also possible to detect the three-dimensional extension of an organ or body surface of the patient, of the medical object and/or of the medical area.

In some embodiments, the set further includes a visualization device. It is suitable and configured to output the result graphically or visually. The visualization device may e.g. be implemented as, or comprise, a printer, plotter, monitor, display.

In some embodiments, the visualization allows diagnostics, for example if the pulse wave propagation in the patient's vascular system is considered by using a set according to exemplary embodiments of the present invention.

Radar technology enables creation of a complete image of the surface of a body with high temporal resolution and thus measurement or detection of the smallest changes of the surface (lateral resolution is determined by the antenna characteristic, distance resolution by the pulse duration or the bandwidth of the emitted signal). By using millimeter waves, for example, a resolution in the micrometer range may be achieved.

Likewise, optical 3D coordinate measuring machines may produce a complete image of the surface of a body (resolution clearly <1 mm—e.g. 0.050 mm), and the sending device(s) and/or receiving device(s) may be implemented accordingly.

If the topology of a surface of a human body is now measured by taking several images in close temporal distance to each other (e.g., a sequence of images), the propagation of the "pulse wave" (e.g. movement of blood) caused by the heart contraction may be tracked through the body. The initial signal of the pulse wave comes from the heart and is detected from there by the sensor system all the way to the extremities.

The speed of propagation, the continuity of the speed of propagation, and the amplitude height of the pulse wave are important indicators for the assessment of the vascular condition (vascular stiffness) of a person and for the identification of sclerotic changes.

Before narrowing (stenoses), the amplitude increases. In contrast, the rate of expansion and amplitude are reduced in vasodilations.

The comparison of the measurement results for both halves of the body (sagittal section) is a further indicator for a possible anomaly of the vascular condition (unequal velocity of propagation, unequal amplitude in the comparison between both sides of the body). The set may also be programmed for such an evaluation.

The sequence may also be composed of individual recordings, which were recorded between successive heartbeats and are subsequently referenced to the heartbeat as the starting point (similar to a "stroboscopic recording"). This considerably reduces the requirements for the temporal resolution of the measurement technology.

Exemplary embodiments of the present invention also include measuring the fistula morphology, the detection of shunt vibrations/shunt blood circulation, in particular the detection of the change in vibration patterns at the fistula over months and years.

By using a set according to exemplary embodiments of the present invention, it is thus possible to obtain information not only about possible diseases of the central vascular system, but also about diseases or changes in the vessels of the extremities. The measuring is contactless and fast, and may also be applied to the entire body or alternatively, it may be limited to individual body areas.

In some embodiments according to the present invention, the set further comprises an identification device, e.g. a backscatter tag. The identification device in turn comprises one or more devices for modulating the radar waves received by it and emitted by the first sending device and for varying or changing the radar waves reflected by it in a manner typical for the identification device. The identification device is preferably provided in order to be worn on the body of a person, in particular the patient. Alternatively or in addition, it may be provided that the identification device can be worn by medical personnel and/or non-medical persons (for example visitors, technicians, cleaning staff, etc.).

Exemplary embodiments of the invention also include providing devices, in particular disposable devices, with an identification device. These may also be comprised by the medical set.

The identification device may be or comprise a radio frequency identification tag (RFID tag).

In some embodiments according to the present invention, the at least one device for modulating has a plurality of resonant circuits.

In certain embodiments, the identification device and/or its modulating devices have an energy source. In other embodiments, the identification device and/or its modulating devices may not have an energy source.

In some embodiments, the set further comprises, or is connected to, a blood treatment apparatus, which comprises a control device for controlling or regulating its function or its operation. For example, the control device may be in signal communication with actuators, sensors or the like of the blood treatment apparatus and, for example, may act on the actuators, such as for example a pump, a valve, etc., depending on a predetermined procedure course and/or depending on signals received from the sensors.

In some embodiments, the output device is programmed to act, by the at least one signal for which it is programmed to output, on the control device, which in turn controls or regulates the operation of the blood treatment apparatus.

Thus, if the sleep phase of the patient who is sleeping during the blood treatment session is recognized for example using sleep pattern recognition, it may be provided to adapt treatment parameters, the ultrafiltration profile, the blood pump rate or other, of the current blood treatment session to the sleep phase. Thus, the medical set may automatically, for example, set a lower UF rate in the deep sleep phases in interaction with the control device of the blood treatment apparatus or initiate such a setting to ensure the patient's recovery or to pursue other goals.

Furthermore, it may be provided to initiate safety measures based on the results of the evaluation by the evaluation unit, for instance the disconnection of the extracorporeal blood circuit, the transition to a safe mode, the triggering of alarms, and/or the changing of alarm limits.

In some embodiments, the output device is programmed to load, allow loading or to call up patient-specific data of a patient examined by the set, e.g. into a control or closed-loop control device of a blood treatment apparatus belonging to the set, e.g. from a storage for patient-specific data, e.g. of the blood treatment apparatus. Alternatively or in addition, it is programmed to initiate a patient-specific setup of the blood treatment apparatus, or to enable or recall settings of the blood treatment apparatus.

Loading, calling up, initiating, releasing and/or retrieving may take place on the basis of (i.e. depending on) the result of the evaluation.

In some embodiments, the set also includes at least one position sensor, which is not configured for measurement by radar waves or does not and/or cannot emit such waves, but measures based on a different measuring or operating principle.

In these embodiments, the evaluation unit is additionally programmed to receive and evaluate signals from the position sensor. The evaluation may consist of or include checking the signals of the position sensor using predetermined criteria. In the simplest case these relate to the question of whether signals from the position sensor (e.g. implemented as a pressure sensor) were received at all. More complex evaluations are also possible.

The evaluation unit is further programmed in these embodiments to cause the first and/or second sending device to emit radar waves only if it has previously determined or if it has also determined that the signals received from the position sensor meet the at least one predetermined criterion.

For example, the at least one position sensor may detect, or contribute to detecting, the position of the patient or of an object (e.g. the position of a backrest).

The at least one position sensor may be, for example, a button, a capacitive sensor, an optical sensor, a temperature sensor or the like. It may detect the presence of the patient at the measurement location, so that a radar measurement is only carried out/evaluated if the patient remains calm and lies, stands or sits in the "right" place. This may increase the quality of the measurement using a set according to exemplary embodiments of the present invention. Furthermore, no radar radiation is emitted if this would not bring about any recognizable benefit.

Thus, for example, problems of electromagnetic compatibility (EMC) of the set may be reduced, because the radar wave sending device does not interfere with other devices by continuous and possibly unintentional, because of being useless, emission of electromagnetic radar waves. An unwanted, mutual interference of the devices arranged in close proximity to each other may thus be reduced to a minimum.

In some embodiments, the set comprises a lying or sitting facility for the patient. The position sensor, if present, may be arranged in, on, or elsewhere to monitor the lying or sitting facility, as may also at least the first or further sending devices and/or receiving devices.

It may thus be provided to detect by the position sensor whether the patient is, for example, on the treatment or examination stretcher, and/or where or how the patient is placed thereon for the upcoming or ongoing examination or treatment. It may further be provided that the sending device(s) only begin to emit radar waves upon receiving a signal from the at least one position sensor, specifically when this signal indicates that the patient has taken a seat, has taken a seat correctly or as desired or where exactly he or parts of special interest of his body are placed on the stretcher.

This two-step or two-stage examination of the patient using the set may advantageously avoid the frustrating and futile expenditure of energy to generate radar waves in cases where the patient is not yet ready for measurement or monitoring by using radar waves, e.g. because he has not yet sat down at all or has not yet assumed his final position on the couch. Furthermore, the two-step examination may advantageously lead to better and more precise evaluation results, since it ensures that the patient has assumed the optimal posture or position for the examination or monitoring.

In some embodiments, the evaluation unit is programmed to identify vibrations of the blood treatment apparatus. In this embodiment, the received, reflected radar waves are preferably examined for an oscillation pattern, an oscillation intensity or another oscillation property by the evaluation unit. The comparison can be compared with stored vibration patterns, vibration intensities or other vibration properties.

A set according to exemplary embodiments of the present invention may thus be used to analyze vibrations of the housing based on the results of its radar sensor system.

Exemplary embodiments of the invention include at least two procedures:

For example, a set according to exemplary embodiments of the present invention may be used as part of a device service, i.e. at moments with time gaps between them, e.g. at each visit of a technician for maintenance/repair again.

Alternatively or in addition, a set according to exemplary embodiments of the present invention may perform—e.g. as a component or add-on to a blood treatment apparatus—an analysis of the blood treatment apparatus (as described above), for example, continuously or frequently, regularly, independently and/or automatically, for example, as part of a preventive or predictive maintenance or self-maintenance.

For this purpose, patterns such as micro-vibration patterns may be measured and compared with reference data sets or data patterns. Changes in frequency, frequency components and/or amplitude heights may be indicators of an existing or developing technical problem with the blood treatment apparatus. For this purpose, pattern matchings or comparisons of one and the same blood treatment apparatus or between blood treatment apparatuses of e.g. the same type and preferably over a longer period of time may be provided.

Exemplary embodiments of the present invention also include, if applicable, monitoring the blood treatment apparatus or a treatment using the same. For example, an incorrectly inserted tube set on the blood pump may be identified using pattern recognition of the reflected radar waves.

Thus, the medical set may be used as a radar sensor or near-field radar sensor in the device or as a "tool" for the technician. It may be used to evaluate the sound patterns and vibrations of the machine from the outside.

Furthermore, it is provided for it to be used for quality control in the production of medical apparatuses, e.g. blood treatment apparatuses.

An advantage of the radar-based proceeding may be that it is not interfered by signals, e.g. optical or acoustic signals, from the environment. Further, vibrations are advantageously detected directly and not by the pressure waves generated by the vibration, as is the case with acoustic methods. Furthermore, a location-sensitive measurement may be carried out, especially if the sending device and/or receiving device are equipped as or with an antenna array.

An advantage of using radar technology may be that in some embodiments the medical set may be used as an optical distance sensor and e.g. the evaluation unit may be programmed accordingly. Hence, it may be provided to measure a distance based on the travel time between the radar waves emitted towards the interface and the reflected radar waves. The temporal resolution of the measurement can be measured for this purpose.

In some embodiments, the first and/or second sending devices each consists of, or comprises, a sender or a sender array.

A sender array is understood to mean an arrangement of spatially separate senders which, due to its arrangement (for example linearly in rows or planar on a surface or level) and the possibility of individually controlling the individual senders in the array, enables directional radiation.

In some embodiments, the first and/or second receiving devices each consists of a receiver or a receiver array or comprises a receiver or a receiver array.

In some embodiments of the medical set, the control device or the closed-loop control device of the blood treatment apparatus is programmed or configured to at least temporarily block the execution of at least one function of the blood treatment apparatus based the reception of the signal from the output device.

In several embodiments, the blood treatment apparatus is implemented as a dialysis apparatus, hemodialysis apparatus, hemofiltration apparatus or hemodiafiltration apparatus, in particular as an apparatus for acute renal replacement therapy, for chronic renal replacement therapy, or for continuous renal replacement therapy (CRRT).

In some embodiments, the medical set is or includes a portable device. In some embodiments, the medical set is suitable for mobile use and may be set up freely in the room, at a patient's bed, etc. In other embodiments, it is, at least in sections thereof, provided e.g. on the ceiling.

In some embodiments, the medical set or a part of it, such as the output device, is in a data technical connection to a central or distributed computing unit, for example via a local area network (LAN), a wireless local area network (WLAN), WiFi, Bluetooth, Near Field Communication (NFC), mobile communication, etc.

Some or all of the embodiments according to the present invention may comprise one, several or all of the advantages listed above and/or below.

A set according to exemplary embodiments of the present invention may be used comparatively very hygienically, since no contact (physical contact) with the patient or with the object of observation is necessary. Hence, surface contamination may be avoided and time and costs for disinfection may thus be reduced or saved completely.

Manipulations on the patient may advantageously be avoided when using a set according to exemplary embodiments of the present invention. Thus, the patient does not have to undress, does not have to wear a bracelet and/or a blood pressure cuff and the like.

Measurements, monitoring, etc. can advantageously be carried out autonomously by a set according to exemplary embodiments of the present invention. This means that a doctor does not necessarily have to be present on site. The setup for this is advantageously simple. Thus, exemplary embodiments of the present invention can help to optimize workflows and save time The sensor system of exemplary embodiments of the present invention may be installed in a chair, a stretcher, a bed or in an existing device or object on which the patient takes a stable or fixed position (e.g. pillow, cushion or pad for the arm rest or the like) and which would be used in the course of treatment anyway. This advantageously helps to save costs.

Using exemplary embodiments of the present invention, several patients may advantageously be measured from one position with the same sensor, as long as they are within the range of the sensor. This can help to save material and costs.

A further advantage of exemplary embodiments of the present invention may be the simple protection of the patient's personal rights. When using a set according to exemplary embodiments of the present invention, for example, no film recordings and/or photos are taken which would be detrimental to the anonymity of the patient.

Measurement data may be automated and/or collected over a longer period of time by using exemplary embodiments of the present invention. This may be of particular advantage in the field of home dialysis/SelfCare/SemiCare etc., where the control by medical personnel may be done comparatively less frequently.

All advantages achievable with a method according to exemplary embodiments of the present invention may also be achieved undiminished with apparatuses according to exemplary embodiments of the present invention, and vice versa.

FIG. 1 shows a simplified illustration of a medical set 1000 according to the present invention in a first exemplary embodiment, set up and programmed in order to monitor a patient P and/or a medical or clinical environment or area by radar waves.

The set 1000 comprises at least a first sending device S1 configured to emit radar waves in the direction towards the patient.

The set 1000 further comprises at least a first receiving device E1 for receiving radar waves which were reflected by the patient P.

An evaluation unit A of the set 1000 is configured to evaluate the received radar waves. In this, a result or an evaluation result is achieved and formulated, stored or the like.

The set 1000 further comprises an output device D. It is configured to output the result or at least a signal based on said result, for example to a monitor, a blood treatment device, an alarm device, a data transmission device, a storage device, etc.

In FIG. 1, the set 1000 is shown when monitoring the patient P. Instead of or in addition to patient P, the set 1000 may be used to monitor an object (such as a cannula, patch, etc.) and/or a medical area (such as surfaces, treatment apparatuses, etc.).

FIG. 1 shows the first sending device S1 and the first receiving device E1 of the set 1000 as separate devices of the set 1000. Alternatively, however, exemplary embodiments of the present invention also provide that the first sending device S1 and the first receiving device E1 may be jointly provided, for example as a common component, in a common housing, on the same chip, etc.

The output device D may include a display or may output signals to a visualization device V (such as a display), to an alarm device or the like.

Figure 2:
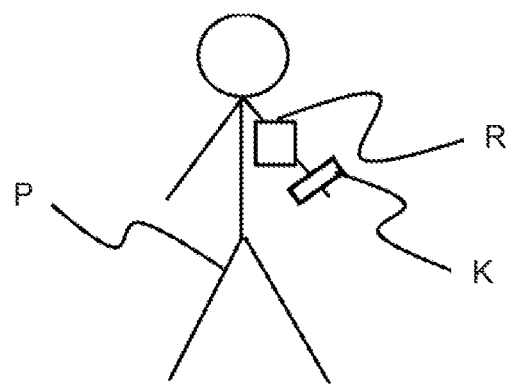
FIG. 2 shows a simplified illustration of a patient with a reference object as part of a medical set according to the present invention in a second embodiment.

FIG. 2 shows a simplified illustration of the use of a reference object R, which may be part of the medical set 1000 according to the present invention in a second exemplary embodiment.

The reference object R may serve the evaluation unit A in evaluating the received radar waves, by giving an indication of how the patient, his extremity or an object being monitored is positioned, e.g. based on its shape and its detected position. Thus, as in the example shown in FIG. 2, the reference object R may be provided in addition to a cannula K, which provides access to the vascular system of the patient P in the crook of the arm or by a shunt. A possible, exemplary use of the reference object R may be that it is placed directly next to or below the cannula K or at a known distance from it, for example by sticking it to the skin of the patient's arm. If, during the monitoring of patient P, his position/location changes (in particular in relation to the reference object R), and here specifically the arrangement of his vascular access by the cannula K, then if the change in distance is detected by the set 1000 according to exemplary embodiments of the present invention, it is to be feared that cannula K is no longer located where it was first placed by the physician. Such an ascertainment or identification by the evaluation unit A may lead to an alarm triggered by the output device D.

Figure 3:
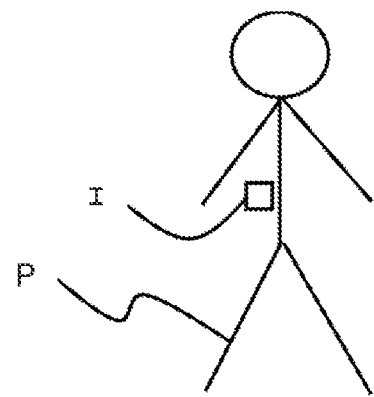
FIG. 3 shows a simplified illustration of a patient with an identification device as part of a medical set according to the present invention in a third embodiment.

FIG. 3 shows a simplified illustration of the medical set 1000 according to the present invention in a third exemplary embodiment with an identification device I as described herein. For possible implementations of this embodiment, reference is made to the above-mentioned statements.

Figure 4:
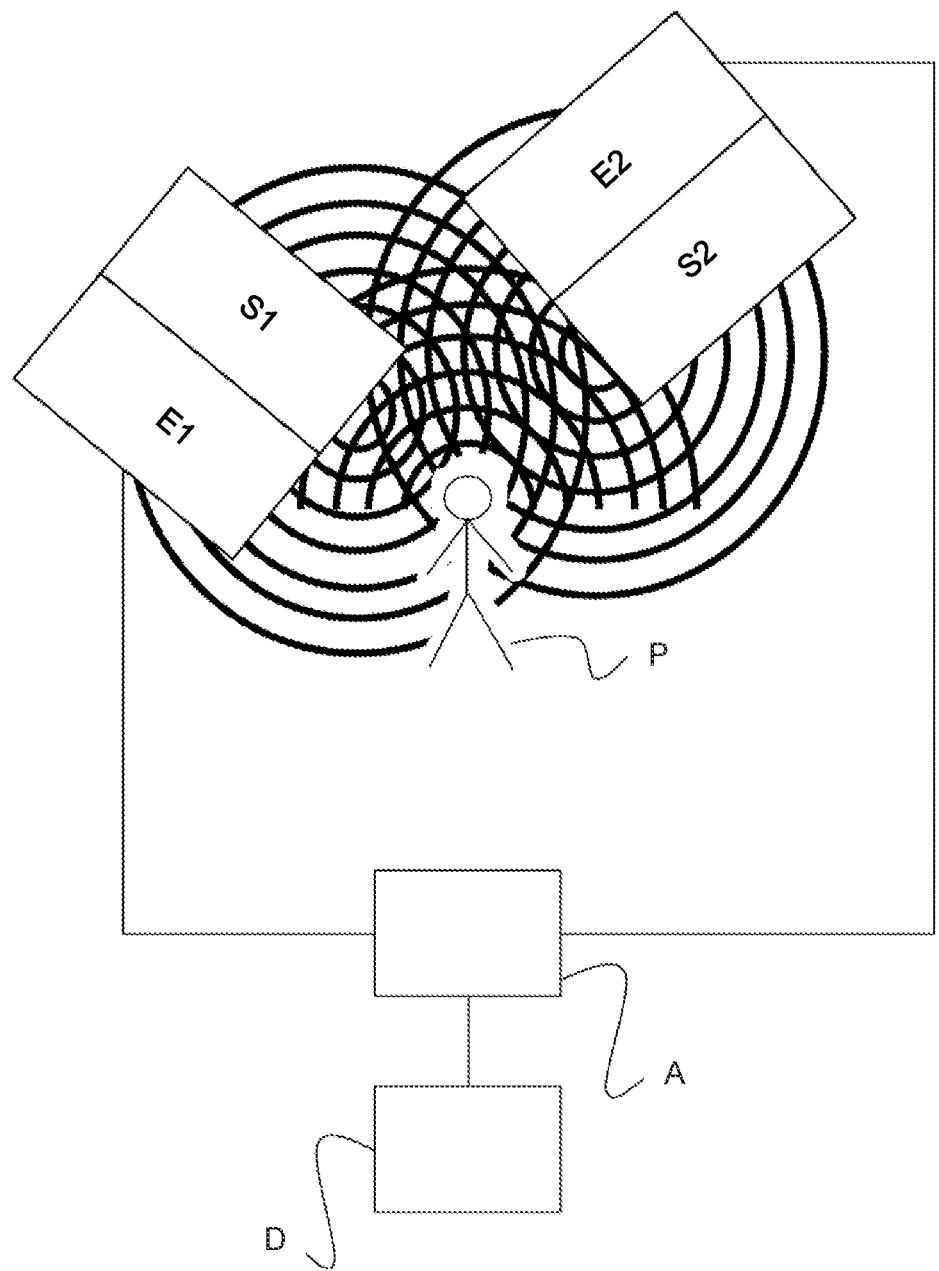
FIG. 4 shows a simplified illustration of a medical set according to the present invention in a fourth embodiment.

FIG. 4 shows a simplified illustration of the medical set 1000 according to the present invention in a fourth exemplary embodiment.

In addition to the first receiving device E1 and the first sending device S1 already shown in FIG. 1, the set 1000 shown in FIG. 4 also comprises a second receiving device E2 and a second sending device S2.

In this, the first sending device S1 and the first receiving device E1 are arranged elsewhere than the second sending device S2 and the second receiving device E2.

The patient P, or alternatively a medical area or medical object, is thus irradiated by radar waves from different directions, or from different locations, by the two sending devices S1, S2, and the respective reflected radar waves are received by the two receiving devices E1, E2 from different directions or from different locations.

The evaluation unit A may be programmed to create a three-dimensional or approximate three-dimensional view of the patient, medical area or object from the signals transmitted to it by the two receiving devices E1, E2. The (approximate) three-dimensional view may be, for example, displayed by the output device D.

Figure 5:
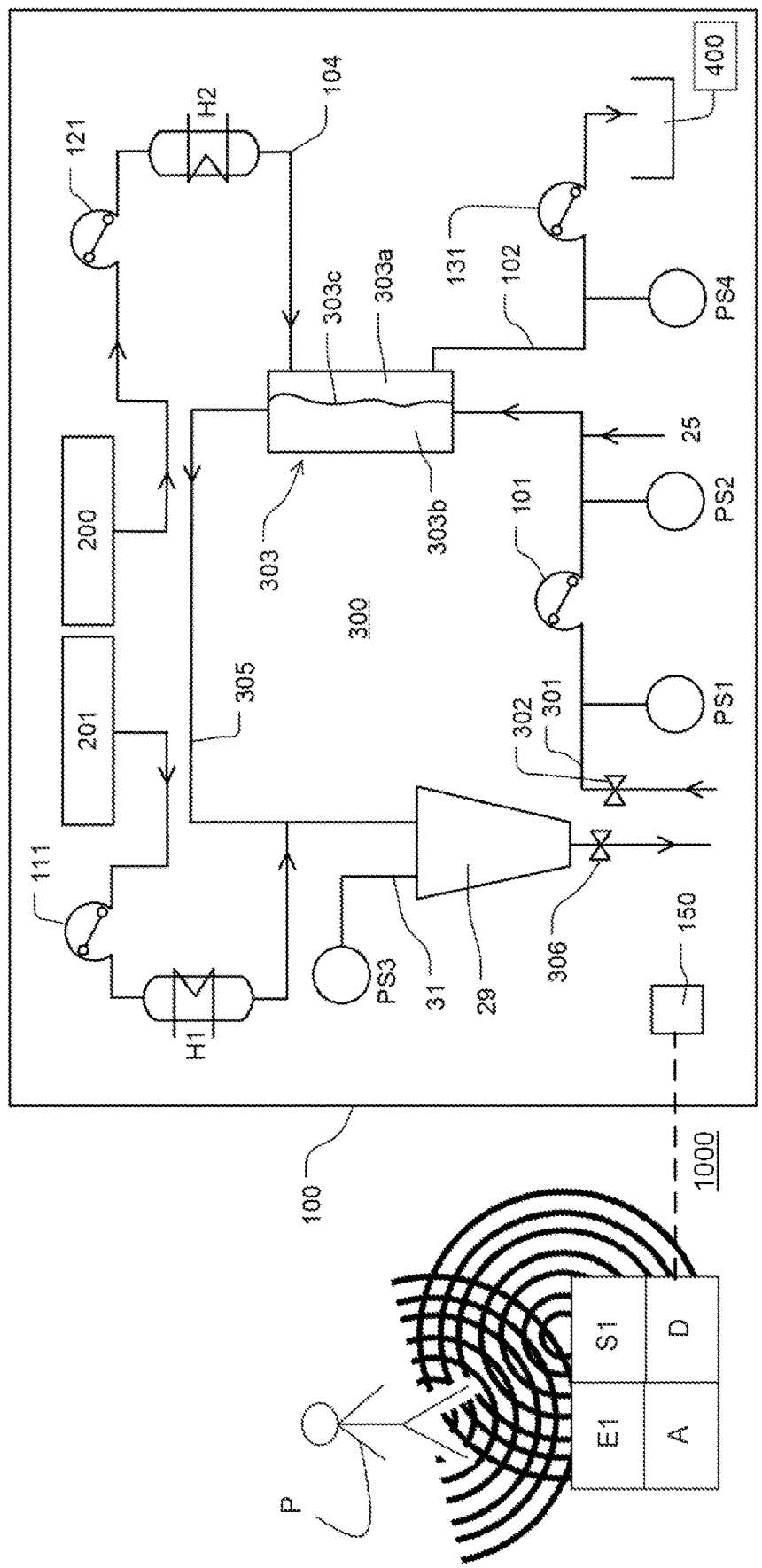
FIG. 5 shows a simplified illustration of a medical set with a blood treatment apparatus according to the present invention in a fifth embodiment.

FIG. 5 shows a simplified illustration of a method flow diagram of a blood treatment apparatus 100 of a medical set 1000 according to a fifth exemplary embodiment of the invention.

The blood treatment apparatus 100 may be connected to an extracorporeal blood circuit 300 and to a discharge hose system leading to an effluent bag 400.

The extracorporeal blood circuit 300 comprises a first line 301, here an arterial line section.

The first line 301 is in fluid communication with a blood treatment device, here exemplarily a blood filter or dialyzer 303. The blood filter 303 comprises a dialysis liquid chamber 303a, through which dialysis liquid is led, during use, and a blood chamber 303b through which blood is led during use. The dialysis liquid chamber 303a and the blood chamber 303b are separated from each other by a semi-permeable membrane 303c. Blood and dialysis liquid are mostly led through the blood filter 303 in the counter flow principle.

The extracorporeal blood circuit 300 further comprises at least a second line 305, here a venous line section.

Both the first line 301 as well as the second line 305, serve for their connection to the vascular system of the patient P.

The first line 301 may be connected with a (first) hose clamp 302 for blocking or closing the line 301. The second line 305 may be connected to a (second) hose clamp 306 for blocking or closing the line 305.

The blood treatment apparatus 100 which is represented, in FIG. 1, only by some of its devices and merely schematically, comprises a blood pump 101. During the patient's treatment, the blood pump 101 conveys blood through sections of the extracorporeal blood circuit 300 towards the blood filter or dialyzer 303. This is illustrated by the small arrows, which are used in each of the figures to generally indicate the direction of flow.

Fresh dialysis liquid is pumped from a source 200 along the dialysis liquid inlet line 104 into the dialysis liquid chamber 303a, by a pump for dialysis liquid 121, which may be configured as a roller pump or as an otherwise occluding pump or as a pump of any other type. The dialysis liquid leaves the dialysis liquid chamber 303a towards the effluent bag 400 as dialysate possibly enriched by filtrate. The filtrate may comprise water that has been withdrawn from blood in the blood filter. Dialysate and filtrate are herein individually or collectively denoted simply as effluent.

In the prior art, the effluent is directly discarded via an effluent outlet line 102 or above all in the case of an acute treatment, it is led to an effluent bag 400 and is first stored there. After completion of the blood treatment, or in bag emptying intervals during the blood treatment (intervals in which the effluent bag 400 is emptied), the effluent from the effluent bag 400 is discarded, using a discharge line, into e.g. a sink or a differently designed basin.

The source 200 may be, for example a bag or a container. The source 200 may also be a fluid line through which on-line and/or continuously generated or mixed liquid is provided, for example a hydraulic output or hydraulic connection of the blood treatment apparatus 100.

A further source 201 with substitute may be provided. It may correspond to the source 200 or be a separate source.

In addition to the aforementioned blood pump 101 and the pump 121 for dialysis liquid, the arrangement shown in FIG. 5 may include a series of further pumps, including, for example, pump 111 for substitute, and the pump 131 for the effluent.

The pump 111 is provided to supply the second line 305 with substitute from the source 201, for example a bag (e.g., via a heating bag H1).

The pump 121 is provided to supply the blood filter 303 with dialysis liquid, using a dialysate liquid inlet line 104, from (out of) a source 200, for example out of a bag (e.g., via a heating bag H2).

The thus supplied dialysis liquid exits again from the blood filter 303 via a dialysate outlet line 102 supported by the pump 131, and may be discarded.

Upstream of the blood pump 101, an arterial sensor PS1 may be provided. During a patient's treatment it measures the pressure in the arterial line.

Downstream of the blood pump 101, but upstream of the blood filter 303 and, if provided, upstream of an addition site 25 for heparin or another systemic anticoagulant, a further pressure sensor PS2 may be provided. It measures the pressure upstream of the blood filter 303 ("pre-hemofilter").

Again, a further pressure sensor to measure the filtrate pressure of the blood filter 303 may be provided as PS4 downstream of the blood filter 303, however preferably upstream of the pump 131 in the dialysate outlet line 102.

Blood, which leaves the blood filter 303, may pass through a venous blood chamber 29, which may comprise a de-aeration device 31 and/or a further pressure sensor PS3. Subsequently, the blood will be led back to the patient (reinfused).

A control device or closed-loop control device 150 may be configured or (software) programmed for regulating or controlling the blood treatment apparatus 100 for the purpose of performing a blood treatment session. It is in this example part of the blood treatment apparatus 100. In some embodiments, the control device or closed-loop control device 150 may also be provided separate from the blood treatment apparatus 100.

The control device or closed-loop control device 150 may be in wired or wireless signal communication to any of the components of the medical set mentioned herein.

FIG. 5 also shows a simplified illustration of the medical set 1000 in an exemplary embodiment.

The output device D of the set 1000 is connected in signal communication to the control device 150 of the blood treatment apparatus 100 in a wired, wireless or in another manner or is prepared for this purpose, for example by coupling both devices D and 150, for example by pairing, etc.

Pairing is understood as a process that takes place in connection with computer networks to establish an initial link or connection between computer units for the purpose of communication. An example of this is the establishing of a Bluetooth connection, by which various devices (e.g. smartphone, headphones) are connected with each other. Pairing is sometimes also referred to as bonding.

The set 1000 may be programmed to act on the operation of the blood treatment apparatus 100 using the control device 150. For example, if the evaluation unit A has determined that the cannula K of the patient P is no longer correctly positioned or even is dislocated, the output device D can, by sending signals to the control device 150, switch or transfer the blood treatment apparatus 100 into an emergency mode, shut it down, stop the blood pump 101, issue an alarm using the blood treatment apparatus 100 and/or prompt the like.

Figure 6:
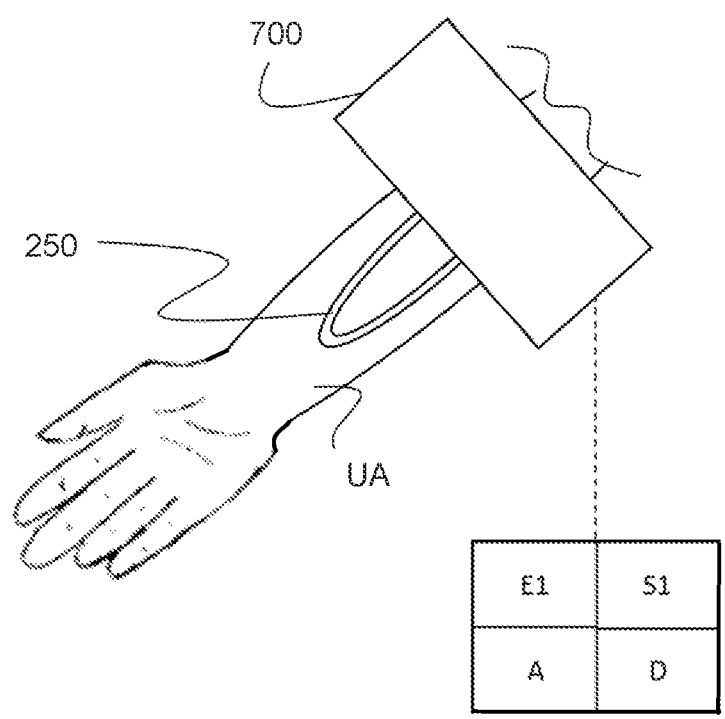
FIG. 6 shows a simplified illustration of a medical set according to the present invention in a sixth embodiment.

FIG. 6 shows a simplified illustration of a medical set 1000 according to the present invention in a sixth exemplary embodiment.

The set 1000 shown in FIG. 6 may include a cannulation robot 700 for automatic and/or mechanical puncture of a vessel on the forearm UA of patient P, here exemplarily a fistula 250 as puncture site. Such a cannulation robot 700 may be part of the medical set 1000 and may be implemented, for example, in accordance with U.S. Patent Publication No. US 2019/0374700 A1, U.S. Pat. No. 5,647,373, U.S. Patent Publication No. 2015/0065916 A1, and U.S. Patent Publication No. 2016/0249990, the disclosures of which are incorporated herein by reference.

The evaluation unit A may be programmed to determine the course of the vessel to be punctured. The output device D may be programmed, in unidirectional or bidirectional connection with the cannulation robot 700, to control or regulate the latter aiming for optimally puncturing the fistula 250 according to predetermined criteria, rules, etc.

Figure 7A:
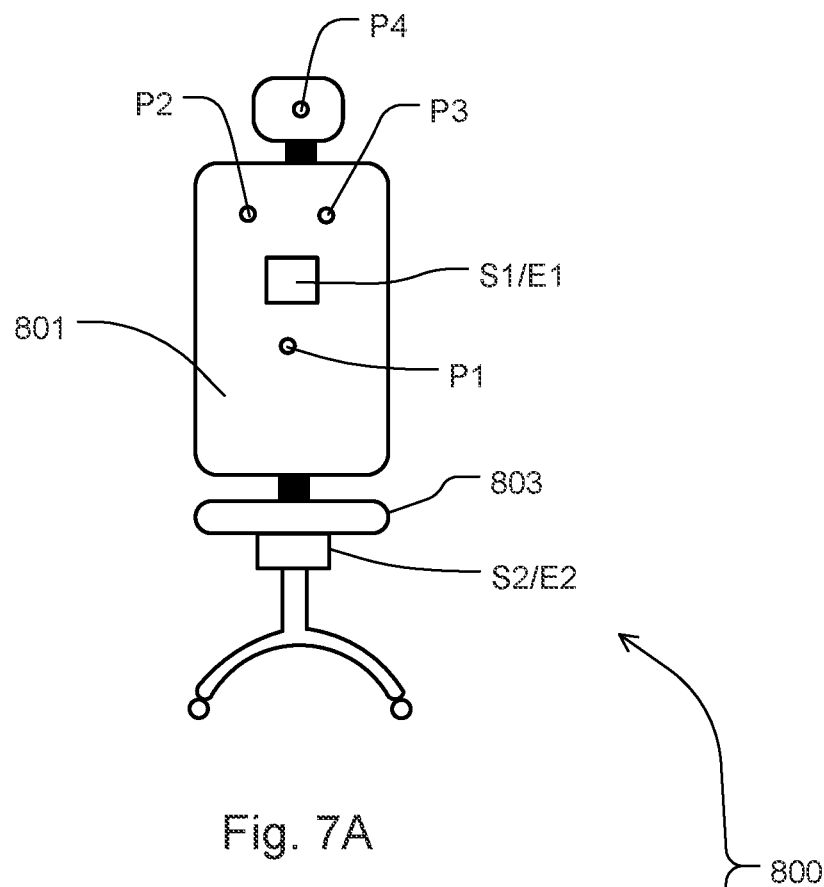
FIG. 7A shows a simplified illustration of front view of a medical set comprising a lying or sitting facility for the patient according to the present invention in a seventh embodiment.
Figure 7B:
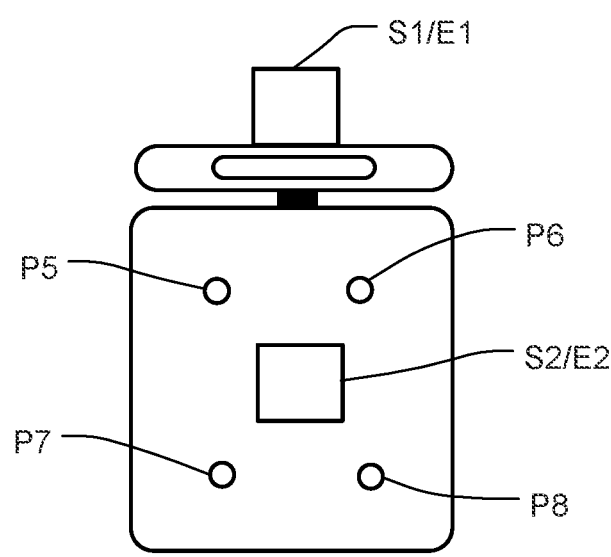
FIG. 7B shows a simplified illustration of a top view of the medical set shown in FIG. 7A.

FIG. 7A and FIG. 7B show simplified illustrations of a medical set 1000 according to the present invention in a seventh exemplary embodiment, which comprises a lying or sitting facility 800 (e.g., a chair, a reclining chair, a bed, or a reclining bed) for patient P. The medical set 1000 comprises at least a first position sensor P1, which is exemplarily arranged in or on the lying or sitting facility 800. The set 1000 is shown from the front in FIG. 7A and from above in FIG. 7B.

A backrest 801 may be seen in which, in addition to the first position sensor P1, further position sensors P2, P2 and P4 may be provided. A seat 803 can also be seen.

The position sensors P1, P2 and P3 detect the position of the patient P, if he/she has been seated on the lying or sitting facility 800. In particular, they detect or determine whether the patient has leaned either completely or at least sufficiently against the backrest 801 and thus taking a firmly defined position in relation to the radio-based first sending device S1 and/or receiving device E1, at least one of which may also be incorporated in the backrest 801.

Alternatively or in addition, a second sending device S2 and a second receiving device E2 may be placed on the lying or sitting facility, for example under the seat 803. Several of these device combinations allow a more accurate detection of the position of the patient P when said patient has taken place on the lying or sitting facility 800.

FIG. 7B shows the lying or sitting facility 800 shown in FIG. 7A with a view on the seat surface 803 from above.

In the seat 803, position sensors P5 to P8 may be provided in addition or alternatively to the position sensors P5 to P8 in the backrest 801 (or assigned to it), in each case in the number shown here, or in smaller or larger numbers.

The function of the position sensors P5 to P8 corresponds to that of position sensors P1 to P4.

Figure 8:
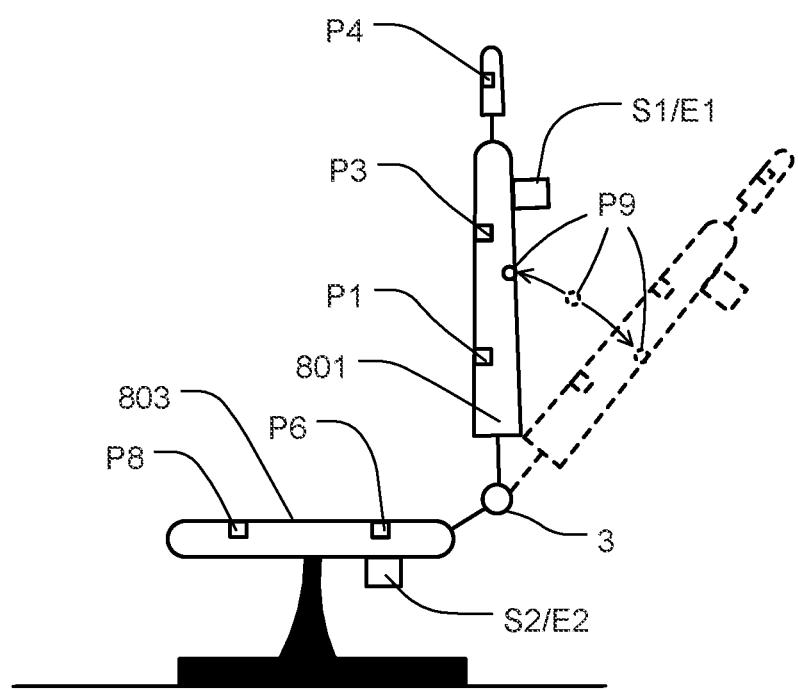
FIG. 8 shows a simplified illustration of a side view of a medical set which comprises a different lying or sitting facility for the patient according to the present invention in an eighth embodiment.

FIG. 8 shows a simplified illustration of a medical set 1000 according to the present invention in an eighth exemplary embodiment, which comprises a lying or sitting facility 800, shown from the side, for the patient P. The medical set 1000 in turn has at least a first position sensor P1, which is herein exemplarily arranged in or on the lying or sitting facility 800. The set 1000 is shown from the side in FIG. 8.

As an alternative to, or in addition to, the position sensors P1 to P8 already known from FIGS. 7A and 7B, the position of the backrest 801 may be detected by a position sensor P9. If or when the patient P is completely seated on the lying or sitting facility 800 and leans against it as usual, the backrest 803 is pushed back by the weight of said patient. The position sensor P9, which may alternatively be configured as an angle sensor, can recognize this.

In order to determine useful vital data or other measurements on patient P, it is helpful to know the exact position of the patient. For this purpose, sensors such as the position sensors P1 to P8 for position detection or the position sensor P9 as angle sensor may be used, which might be simple and inexpensive (electrical switches, force sensors, proximity sensors, etc. Such position sensors are provided, for example, in the lying or sitting facility 800, the patient bed or the chair.

Feedback from the position sensors P1 to P9 may be used according to exemplary embodiments of the invention in order to activate the sending device(s) S1, S2 only when the patient P is actually in the measuring field. This prevents electromagnetic radar waves from being emitted or sent freely into the room without the patient P being reasonably or usefully examined or any other objective being pursued. Problems caused by electromagnetic waves freely emitted into the room may thus be avoided/reduced. Energy is saved because the sending devices S1, S2 are only active when a measurement can be carried out in a reasonable or useful way (e.g. the patient P is sitting on a chair).

It will be appreciated that the execution of the various machine-implemented processes and steps described herein may occur via the execution, by one or more respective processors, of processor-executable instructions stored on a tangible, non-transitory computer-readable medium, such as random access memory (RAM), read-only memory (ROM), programmable read-only memory (PROM), and/or another electronic memory mechanism. Thus, for example, operations performed by a medical device, a medical system, or other devices as discussed herein may be carried out according to instructions stored on and/or applications installed on one or more respective computing devices.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The invention claimed is:

1. A medical system, comprising:
   a transmitter;
   a receiver;
   a processor;
   an output interface;
   a memory having processor-executable instructions stored thereon; and
   a blood treatment apparatus comprising a control device;
   wherein the processor-executable instructions comprise instructions which, when executed by the processor, provide for performance of the following by the medical system:
   emitting, by the transmitter, radar waves using one or more predetermined frequencies;
   receiving, by the receiver, reflected radar waves;
   determining, based on the reflected radar waves, that a cannula for a patient being treated by the blood treatment apparatus is no longer correctly positioned; and
   based on the cannula being incorrectly positioned, sending, via the output interface, signals to the control device to switch the blood treatment apparatus into an emergency mode, to shut down the blood treatment apparatus, and/or to stop a blood pump of the blood treatment apparatus.

2. The medical system according to claim 1, wherein the processor-executable instructions further comprise instructions which, when executed by the processor, provide for performance of the following by the medical system:
   determining vital data or a state of a vessel of the patient.

3. The medical system according to claim 1, wherein the processor-executable instructions further comprise instructions which, when executed by the processor, provide for performance of the following by the medical system:
   determining a state of a vessel of the patient based on capturing and/or evaluating pulse wave propagation at or within the vessel.

4. The medical system according to claim 1, wherein the processor-executable instructions further comprise instructions which, when executed by the processor, provide for performance of the following by the medical system:
   identifying a person based on vital data, body topology, and/or movement patterns.

5. The medical system according to claim 1, further comprising:
   a reference object attached to the patient's body;
   wherein the processor-executable instructions further comprise instructions which, when executed by the processor, provide for performance of the following by the medical system:

evaluating radar waves reflected from the reference object and received by the receiver.

6. The medical system according to claim 1, wherein the processor-executable instructions further comprise instructions which, when executed by the processor, provide for performance of the following by the medical system:
comparing the reflected radar waves received by the receiver or evaluations based thereon with reference data, reference sets and/or reference samples.

7. The medical system according to claim 6, wherein the reference data, reference sets and/or reference samples comprise data, data sets and/or samples relating to respective materials, surfaces, tissues, liquids, radar waves received at another time point, or evaluations based thereon.

8. The medical system according to claim 7, wherein the respective surfaces comprise the patient's skin;
wherein the respective tissues comprise blood vessels; and/or
wherein the respective liquids comprise blood.

9. The medical system according to claim 1, further comprising:
a second transmitter;
wherein the processor-executable instructions further comprise instructions which, when executed by the processor, provide for performance of the following by the medical system:
emitting radar waves in a first direction or from a first location; and
emitting radar waves in a second direction different from the first direction or from a second location different from the first location.

10. The medical system according to claim 1, further comprising:
a second receiver;
wherein the processor-executable instructions further comprise instructions which, when executed by the processor, provide for performance of the following by the medical system:
receiving radar waves from a first direction or from a first location; and
receiving radar waves from a second direction different from the first direction or from a second location different from the first location.

11. The medical system according to claim 1, wherein the processor-executable instructions further comprise instructions which, when executed by the processor, provide for performance of the following by the medical system:
determining a three-dimensional extension of at least one part of the patient being irradiated with radar waves.

12. The medical system according to claim 1, further comprising:
a visualization device;
wherein the processor-executable instructions further comprise instructions which, when executed by the processor, provide for performance of the following by the medical system:
visually outputting an evaluation result.

13. The medical system according to claim 1, further comprising:
an identification device;
wherein the processor-executable instructions further comprise instructions which, when executed by the processor, provide for performance of the following by the medical system:
modulating radar waves emitted by the transmitter toward the identification device.

14. The medical system according to claim 13, wherein the identification device is worn on the patient's body.

15. The medical system according to claim 13, wherein the identification device comprises a plurality of resonant circuits.

16. The medical system according to claim 1, wherein the processor-executable instructions further comprise instructions which, when executed by the processor, provide for performance of the following by the medical system:
providing patient-specific data or a patient-specific setup to the blood treatment apparatus for enabling treatment settings or treatment options to be configured based on a result of an evaluation.

17. The medical system according to claim 1, further comprising:
a position sensor;
wherein the processor-executable instructions further comprise instructions which, when executed by the processor, provide for performance of the following by the medical system:
receiving signals from the position sensor; and
controlling the transmitter to only emit radar waves based on the signals received from the position sensor meeting predetermined criteria.

18. The medical system according to claim 17, wherein the position sensor is arranged in or on an apparatus which is in contact with the patient during the course of a treatment for the patient.

19. A medical system, comprising:
a transmitter;
a receiver;
a processor;
an output interface;
a reference object; and
a memory having processor-executable instructions stored thereon;
wherein the processor-executable instructions comprise instructions which, when executed by the processor, provide for performance of the following by the medical system:
emitting, by the transmitter, radar waves using one or more predetermined frequencies;
receiving, by the receiver, reflected radar waves, wherein the reflected radar waves include radar waves reflected off a first object and radar waves reflected off the reference object;
determining, based on the reflected radar waves, a change in distance between the first object and the reference object; and
based on detecting the change in distance between the first object and the reference object, triggering an alarm.

20. The medical system according to claim 19, wherein the first object is a cannula, and wherein the reference object is placed on a patient at a predetermined distance from the first object.

21. A medical system, comprising:
at least two transmitters, including a first transmitter and a second transmitter;
at least two receivers, including a first receiver and a second receiver;
a processor;
an output interface; and
a memory having processor-executable instructions stored thereon;

wherein the processor-executable instructions comprise instructions which, when executed by the processor, provide for performance of the following by the medical system:
emitting, by the first and second transmitters, radar waves using one or more predetermined frequencies from different directions or different locations;
receiving, by the first and second receivers, reflected radar waves from different directions or different locations;
creating, based on the reflected radar waves, a three-dimensional view of a patient, a medical area, or an object; and
displaying, via the output interface, the three-dimensional view.

22. The medical system according to claim 21, wherein the processor-executable instructions further comprise instructions which, when executed by the processor, provide for performance of the following by the medical system:
detecting oscillations of a blood treatment apparatus.

23. The medical system according to claim 21, further comprising:
a thermal camera;
wherein the processor-executable instructions further comprise instructions which, when executed by the processor, provide for performance of the following by the medical system:
detecting, using the thermal camera, changes in temperature caused by moisture being heated by the radar waves emitted from the transmitter.

24. The medical system according to claim 1, further comprising:
a cannulation robot;
wherein the processor-executable instructions further comprise instructions which, when executed by the processor, provide for performance of the following by the medical system:
determining, based on the reflected radar waves, a course of a vessel to be punctured by the cannulation robot; and
controlling or regulating, via the output interface, the cannulation robot to aim the cannulation robot based on the determined course of the vessel.

25. The medical system according to claim 1, further comprising:
a chair or bed for the patient, wherein the chair or bed comprises a backrest portion and a seat portion;
wherein a first plurality of position sensors, the transmitter, and the receiver are disposed in the backrest portion;
wherein a second plurality of position sensors, a second transmitter, and a second receiver are disposed in the seat portion;
wherein the processor-executable instructions further comprise instructions which, when executed by the processor, provide for performance of the following by the medical system:
determining a position of the patient based on position information from the first and second pluralities of position sensors and based on reflected radar waves received by the first and second receivers.

* * * * *